United States Patent
Jin et al.

(10) Patent No.: US 6,858,408 B2
(45) Date of Patent: Feb. 22, 2005

(54) RECOMBINANT PLASMID PDSBCM, MICROORGANISMS TRANSFORMED THEREWITH, AND METHOD FOR PRODUCING AN ALKALINE PROTEASE VAPK

(75) Inventors: Ghee Hong Jin, Seoul (KR); Hyune Hwan Lee, Yongin-shi (KR); Hyune Mo Rho, Seoul (KR); Hyung Seok Kim, Inchon (KR)

(73) Assignee: Cheil Jedang Corporation, Seoul (KR)

( * ) Notice: Subject to any disclaimer, the term of this patent is extended or adjusted under 35 U.S.C. 154(b) by 23 days.

(21) Appl. No.: 10/333,261

(22) PCT Filed: Jul. 19, 2001

(86) PCT No.: PCT/KR01/01232
§ 371 (c)(1),
(2), (4) Date: Jan. 17, 2003

(87) PCT Pub. No.: WO02/06494
PCT Pub. Date: Jan. 24, 2002

(65) Prior Publication Data
US 2004/0009575 A1 Jan. 15, 2004

(30) Foreign Application Priority Data
Jul. 19, 2000 (KR) .................................. 10-2000-41212

(51) Int. Cl.$^7$ .......................... C12P 21/06; C12P 19/34; C12N 1/20; C12N 15/00
(52) U.S. Cl. .................. 435/69.1; 435/91.1; 435/252.3; 435/252.33; 435/320.1
(58) Field of Search ............................. 435/69.1, 91.1, 435/252.3, 252.33, 320.1

(56) References Cited

U.S. PATENT DOCUMENTS 4,966,846 A    10/1990   Deutch et al.

FOREIGN PATENT DOCUMENTS

KR        00-65867        11/2000

*Primary Examiner*—Mark Navarro
(74) *Attorney, Agent, or Firm*—Burns, Doane, Swecker & Mathis, L.L.P.

(57) ABSTRACT

The invention relates to recombinant plasmid pDSBCm harboring the gene vapk-repeated region, which gene encodes alkalic protease VapK, a microorganism *Vibrio metschnikovii* transformed therewith, and method for producing an alkaline protease VapK using the same microorganism.

6 Claims, 9 Drawing Sheets

RECOMBINANT PLASMID PDSBCM, MICROORGANISMS TRANSFORMED THEREWITH, AND METHOD FOR PRODUCING AN ALKALINE PROTEASE VAPK

TECHNICAL FIELD

The present invention relates to a recombinant plasmid vector pDSBCm comprising the gene vapk dimer, which gene encodes an alkaline protease VapK, a microorganism *Vibrio metschnikovii* transformed therewith, and a method for producing an alkaline protease VapK using the same microorganism.

BACKGROUND ART

In general, an alkaline protease derived from *Vibrio* sp. is referred to as an enzyme that degrades proteins into amino acids and small peptides under alkaline condition, and many microorganisms, such as *Bacillus* sp. and *Serratia* sp., are well-known to excrete alkaline protease.

The most important factor in producing alkaline protease using said microorganisms is the high productivity of alkaline protease, which affects the costs of producing process.

According to the recent inventions, in order to raise the productivity of alkaline protease, recombinant vectors comprising the gene encoding alkaline protease were prepared using genetic engineering techniques and transformants therewith were prepared.

The present inventors previously filed a patent application (KR 1999-12588) titled "alkaline protease VapK useful as laundry detergent, vapk gene, recombinant expression vector, and transformed microorganism", in which the microorganism is *Vibrio metschnikovii* KS1 and the recombinant expression vector is pSBCm. The same microorganism and recombinant expression vector are also used in the present invention.

The present inventors have studied and tested intensively and extensively in order to produce the transformed microorganism with high activity of alkaline protease, and prepared a recombinant plasmid vector comprising the alkaline protease gene doubly, isolated from *Vibrio metschnikovii* KS1 and transformed *Vibrio metschnikovii* with the said recombinant plasmid vector, thereby the transformed microorganism with improved protease activity was produced.

SUMMARY OF THE INVENTION

The present invention provides a recombinant plasmid vector pDSBCm comprising the vapk gene doubly, which gene encodes an alkaline protease.

The present invention also provides a method for producing the said recombinant plasmid vector pDSBCm. The method for producing the recombinant plasmid vector pDSBCm comprises the steps of:

inserting the par gene into a recombinant plasmid vector pSBCm comprising the vapk gene encoding an alkaline protease to prepare a recombinant plasmid vector pSP1, wherein the par gene has the function of improving the stability of the plasmid vector;

orienting the gene vapk of the recombinant plasmid vector pSP1 in reverse direction to prepare a recombinant plasmid vector pSPR1;

digesting the gene between the vapk gene and par gene of pSPR1 with EcoR I, treating with exonuclease Bal31, and ligating them with a ligase to prepare a plasmid vector pSPR1-47 with decreased length; and digesting the plasmid vector pSPR1-47 with Hind III and inserting the gene vapk into the pSPR1-47 digested with Hind III, Also, the present invention provides a transformed host cell comprising said recombinant plasmid vector pDSBCm.

Furthermore, the present invention provides a transformed host cell, which host cell comprises *Escherichia coli* or *Vibrio metschnikovii*.

The present invention also provides a method for producing an alkaline protease VapK using said transformed host cell.

BRIEF DESCRIPTION OF DRAWINGS

Hereinafter, the present invention is described in detail by referring to the attached drawings.

DETAILED DESCRIPTION OF THE INVENTION

The present invention provides a microorganism transformed with a recombinant plasmid vector comprising the gene dimer encoding an alkaline protease VapK, and a method for producing an alkaline protease VapK using said microorganism in higher yield.

The term "the gene dimer" as used herein, means that the two genes with the same nucleotide sequence are operably linked together.

In the present invention, the gene encoding the alkaline protease is isolated by the following steps: culturing *Vibrio metschnikovii* KS1, centrifuging and recovering the cells of *Vibrio metschnikovii* KS1, disrupturing the cells and centrifuging them to obtain the cell-free supernatent, and extracting the chromosomal DNA of *Vibrio metschnikovii* KS1 from the cell-free supernatant. Using said chromosomal DNA of *Vibrio metschnikovii* KS1, the transformed *Escherichia coli* was prepared, that is, by digesting said chromosomal DNA of *Vibrio metschnikovii* KS1 with restriction enzymes like Hind III to produce DNA fragment, cloning the DNA fragment into plasmid vectors to construct pSBCm, pSP1, pSPR1, pSPR1-47 and pDSBCm, and transforming them into *E. coli*.

First, the expression of the alkaline protease was conducted by using the above recombinant *E. coli* comprising plasmid vector pSBCm, and the expression level of the alkaline protease produced from the transformed *E. coli* under alkaline condition was measured. On the basis of this result, the expression of the alkaline protease from said transformed *E. coli* was low as known previously.

In order to solve the above problem, the present inventors cloned the recombinant plasmid vector pDSBCm into *Vibrio metschnikovii* KS1 to produce *Vibrio metschnikovii* pDSBCm. As a result, the activity of the alkaline protease expressed from *Vibrio metschnikovii* pDSBCm was 2.5 times higher than that of the alkaline protease expressed from the host strain *Vibrio metschnikovii* KS1.

The strain *Vibrio metschnikovii* KS1 that was deposited with the Korean Culture Center of Microorganisms, Seoul, Korea as Accession Number of KFCC-10141 on Dec. 15, 1998, which was used in this invention, is produced by treating *Vibrio metschnikovii* RH 530 N-4-8 with N,N-nitrosoquanidine(NTG) as a mutagen, and that was deposited with the Korean Culture Center of Microorganisms as Accession Number of KFCC-11030 on Feb. 23, 1998. As a result, the amount of the alkaline protease produced from the *V. metschnikovii* KS1 was twice as high as that of the strain *V. metschnikovii* RH 530 N-4-8.

Also, the strain *E. coli* Top10F' containing the recombinant plasmid vector pSBCm of the present invention was deposited with the Korean Culture Center of Microorganisms on Dec. 15, 1998, as Accession No. KCCM-10142.

Hereinafter, the more detailed description on the specific effect of the present invention will be given by the following Examples, without limiting the spirit and scope of the invention.

EXAMPLES

Example 1
Cloning of the Alkaline Protease Gene Vapk

Figure 1:
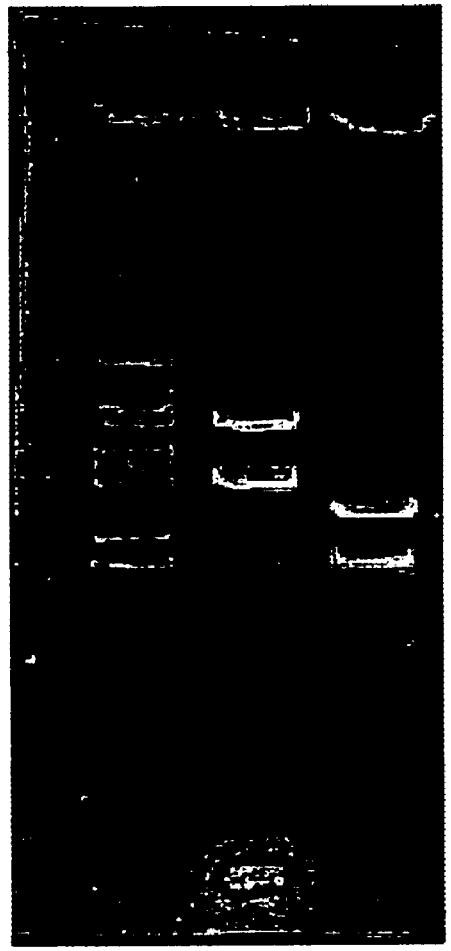
FIG. 1 illustrates the result of electrophoresis of the recombinant plasmid vector pSBCm comprising the vapk gene encoding an alkaline protease. Line M represents size markers, line 1 represents a recombinant plasmid vector pSBCm, and line 2 represents the recombinant plasmid vector pSBCm/Hind III consisting of a vehicle vector pKF3 of 2.2 kb and a Vibrio alkaline protease gene of 2.9 kb.

After culturing the *Vibrio metschnikovii* KS1 in a LSC medium with the composition of Table 1 at 30° C., the grown cells were harvested and disruptured. The disruptured solution was centrifuged at 6,000 rpm and the supernatant was collected. The chromosomal DNA of *Vibrio metschnikovii* KS1 was purified from the supernatant and partially digested with Hind III. The fragment was inserted into a vector pKF3 to clone 2.9 kb alkaline protease gene. The resulted recombinant plasmid vector was designated as pSBCm. The recombinant plasmid vector pSBCm was digested with Hind III and subjected to electrophoresis on 1% agarose gel. After electrophoresis, the agarose gel was stained with ethidium bromide as a staining agent. As a result of the above agarose gel electrophoresis, it was verified that the alkaline protease gene was cloned into a plasmid vector. (FIG. 1)

TABLE 1

| Composition of LSC medium | |
|---|---|
| Composition of LSC medium | Amount (g/L) |
| Tryptone | 10 |
| Yeast extract | 5 |
| Sodium chloride | 10 |
| 1 M Sodium carbonate buffer, pH 10.5 | 100 (ml/L) |

Example 2
Isolation and Purification of the Alkaline Protease

Figure 2:
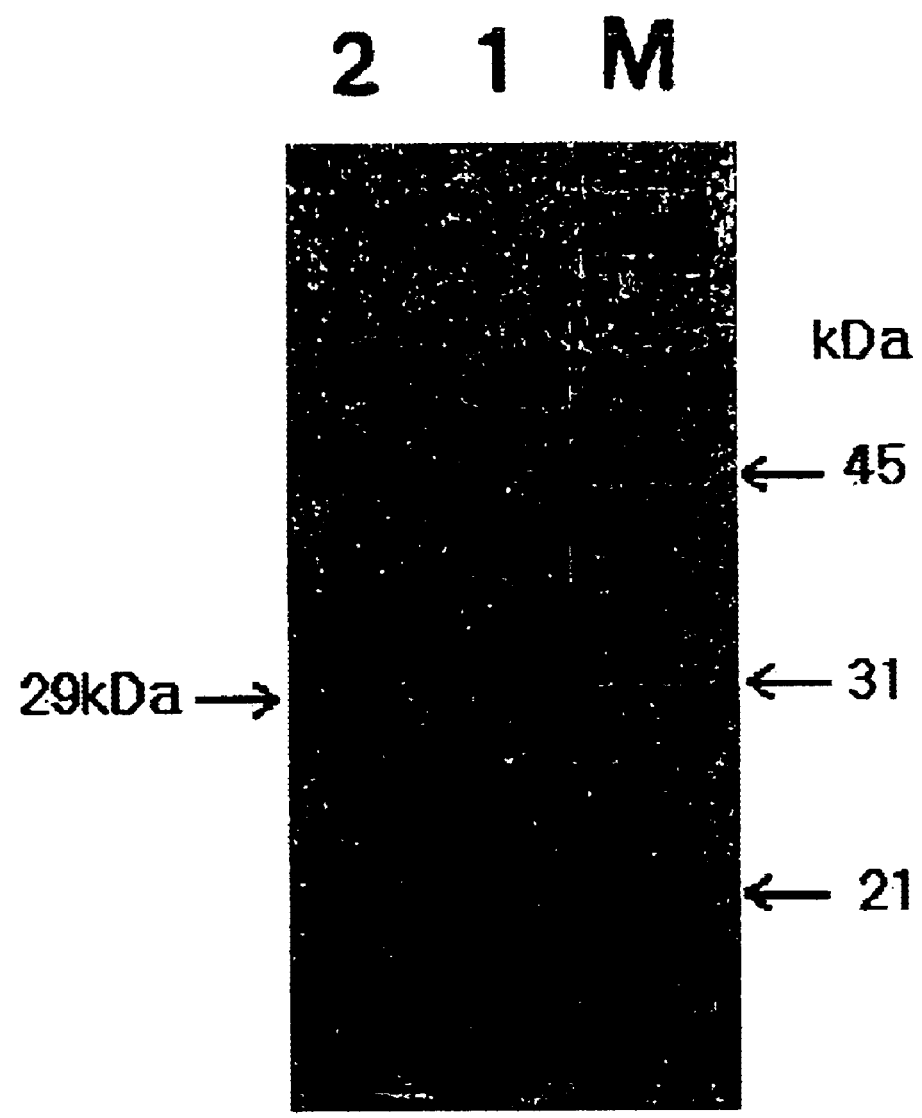
FIG. 2 illustrates the result of SDS-PAGE of each alkaline protease VapK, isolated from both *Vibrio metschnikovii* KS1 and *E. coli* transformed with pSBCm. Line M represents size markers, line 1 represents the alkaline protease expressed by transformed *E. coli,* and line 2 represents the alkaline protease of 29 kDa, expressed by *Vibrio metschnikovii* KS1.

The strain *Vibrio metschnikovii* KS1 cultured in the above LSC medium of example 1 was centrifuged to obtain the supernatant that was used as an enzyme sample of the invention. After culturing the transformed strain *E. coli* pSBCm, the grown cells were harvested and disruptured. The disruptured solution was centrifuged at 6,000 rpm to obtain the supernatant that was also used as another enzyme sample of the invention. Each said enzyme sample was added into a buffer solution consisting of 6M urea, 2.5% sodium dodecyl sulfate, 5% (w/v) beta-mercaptoethanol, 0.01M tris-HCl, pH 6.8, 10% (w/v) glycerol, and 0.002% bromophenol blue in the same ratio. The mixture was heated in boiling water for 15 minutes and subjected to electrophoresis. The finished gel was stained with 0.05% Coomassie Brilliant Blue R-250 and was destained with a mixture of 50% methanol and 10% acetic acid. As a result of SDS-PAGE shown in FIG. 2, a band of the 29 kDa alkaline protease was verified.

Example 3
Activity Assay of Alkaline Protease VapK on Skim Milk Agar

Figure 3:
FIG. 3 illustrates the result of the activity test on the skim milk agar of each alkaline protease VapK, isolated from both *Vibrio metschnikovii* and *E. coli* transformed with pSBCm. Line 1 represents the activity of alkaline protease expressed by the transformed *E. coli* and line 2 represents the activity of alkaline protease expressed by *Vibrio metschnikovii* KS1.
Figure 4:
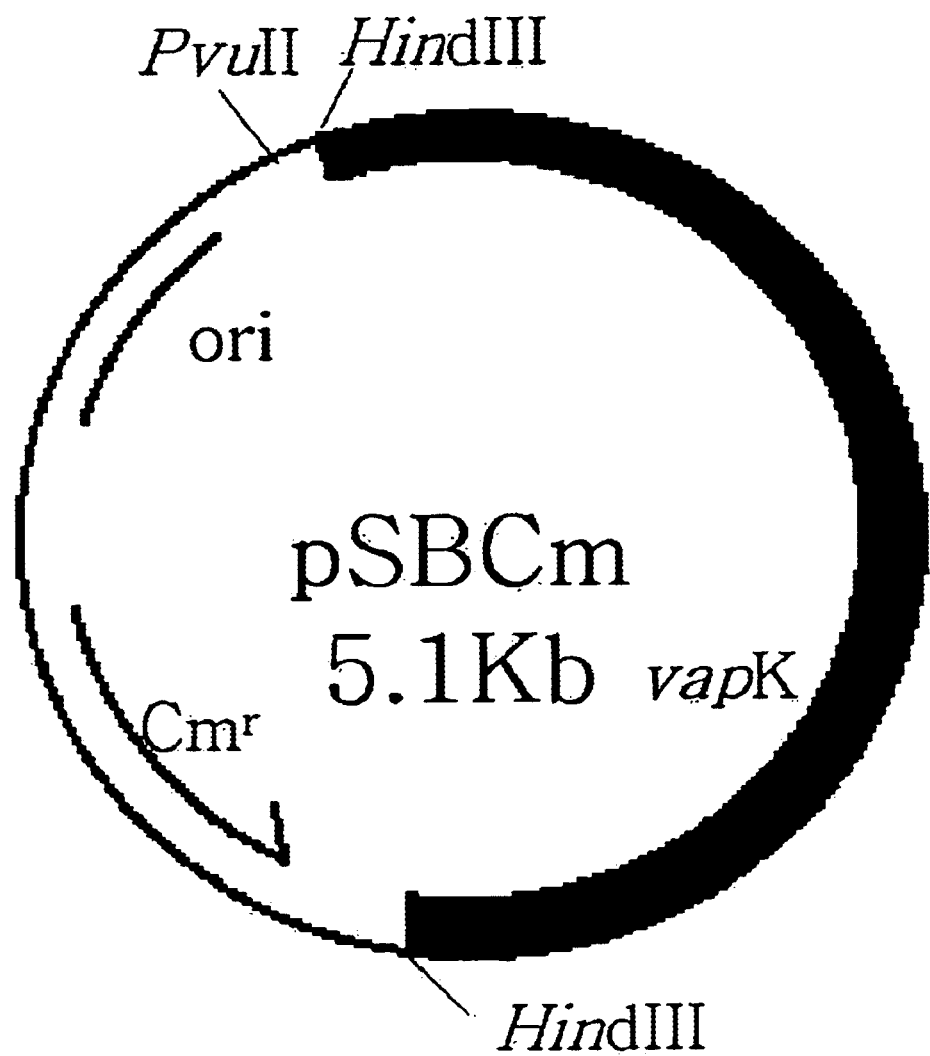
FIG. 4 illustrates the restriction enzyme map of the recombinant plasmid vector pSBCm comprising the alkaline protease gene vapk.

The strain *Vibrio metschnikovii* KS1 cultured in the above LSC medium of example 1 was centrifuged at 6,000 rpm for 10 minutes to obtain the supernatant that was used as an enzyme sample of the invention. After growth of a transformed strain *E. coli* pSBCm, the grown cells were harvested and disruptured. The disruptured solution was centrifuged at 6,000 rpm to obtain the supernatant that was also used as another enzyme sample of the invention. Each said enzyme sample was added into a buffer solution consisting of 50 mM phosphate buffer, pH 7.0, 10% (w/v) glycerol and 0.002% bromophenol blue in the same ratio and the mixture was subjected to native gel electrophoresis. The finished gel was placed on an agar plate containing skim milk and a 50 mM sodium carbonate buffer, pH 10.0 to analyze the activity of the alkaline protease. As a result shown in FIG. 3, the activity of the alkaline protease was verified.

Example 4
Cloning of the Alkaline Protease Gene Dimer

The recombinant plasmid vectors pSP1, pSPR1 and pSPR1-47 were prepared as intermediates in preparation of the recombinant plasmid vector comprising the alkaline protease gene dimer.

Figure 5:
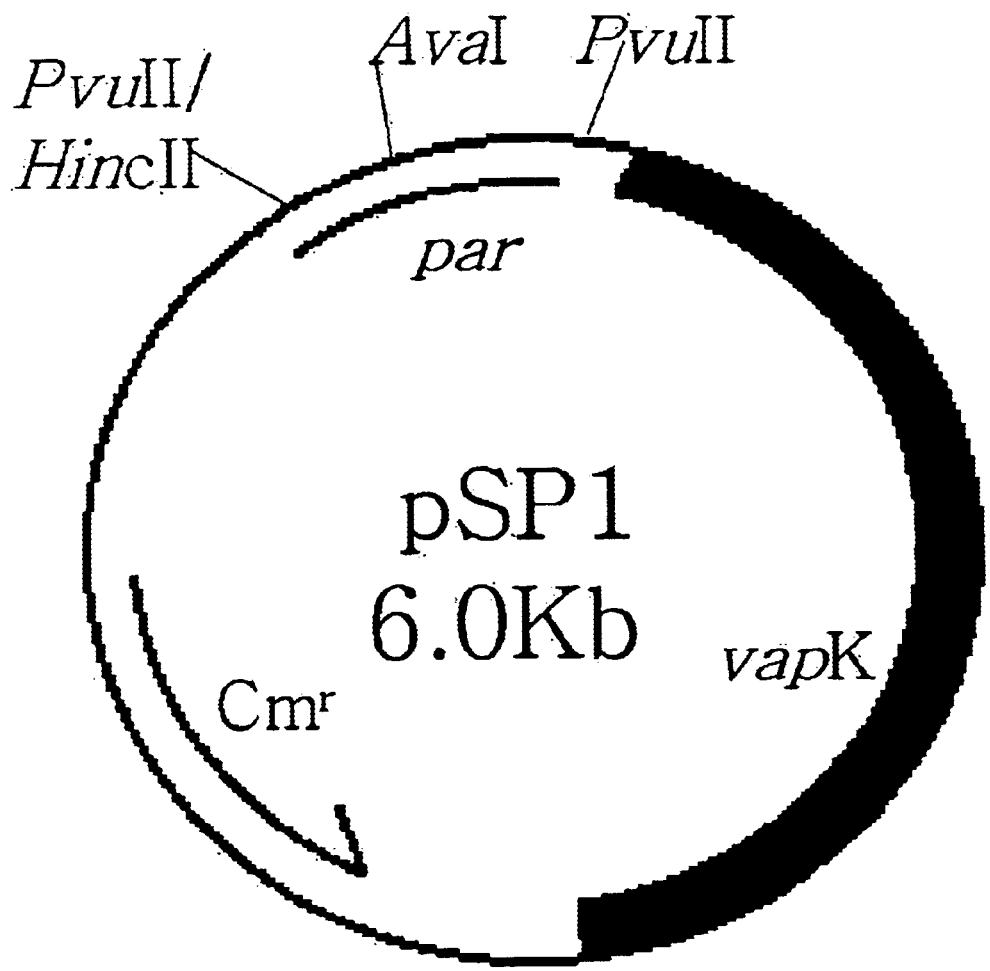
FIG. 5 depicts a restriction enzyme map of the recombinant plasmid vector pSP1 comprising the alkaline protease gene vapk and the par gene.

For the purpose of increasing the stability of the recombinant plasmid vector pSBCm, the gene par was cloned into a region between Pvu II and Hinc II recognition sites of pSBCm to prepare the recombinant plasmid vector pSP1 comprising the alkaline protease gene vapk and the par gene (FIG. 5).

Figure 6:
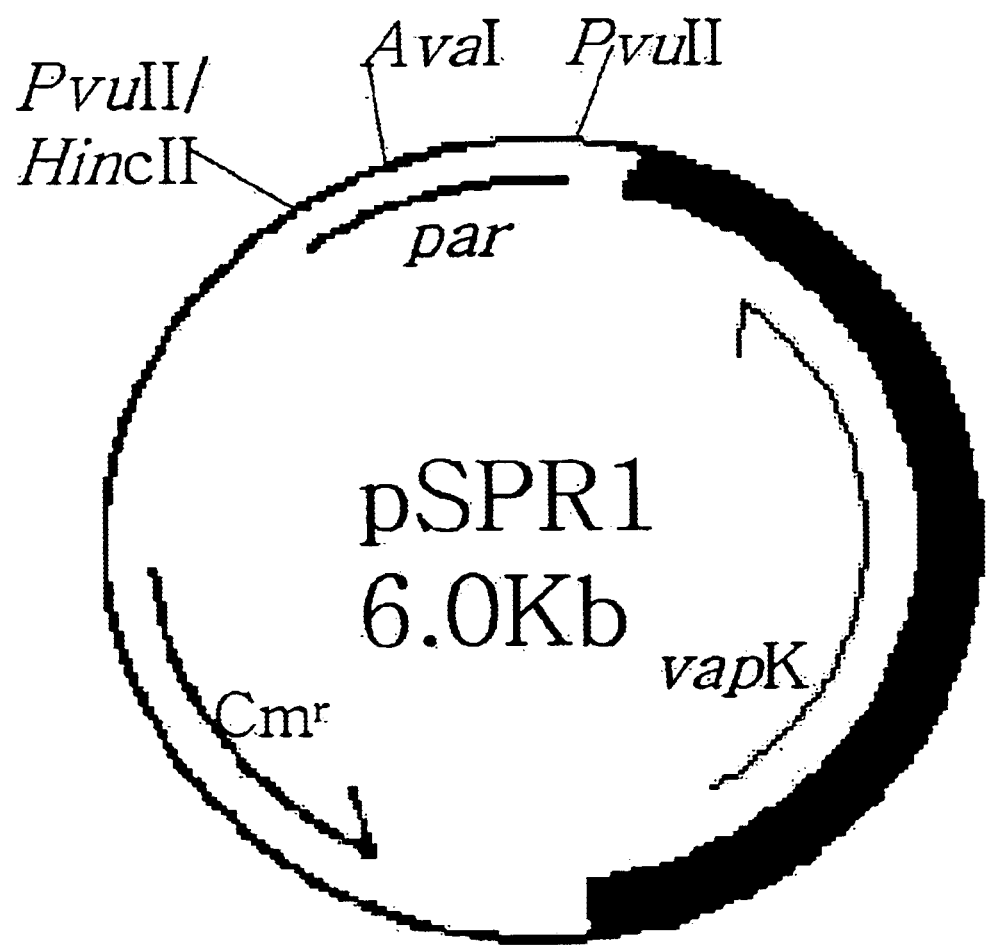
FIG. 6 depicts a restriction enzyme map of the recombinant plasmid vector pSPR1 comprising the par gene and the reverse-oriented alkaline protease gene vapk.

In FIG. 6, the recombinant plasmid vector pSPR1 comprising the reverse-oriented vapk gene and the par gene was prepared as an intermediate in order to reduce the length of the alkaline protease gene vapk in the recombinant plasmid vector pSP1.

Figure 7:
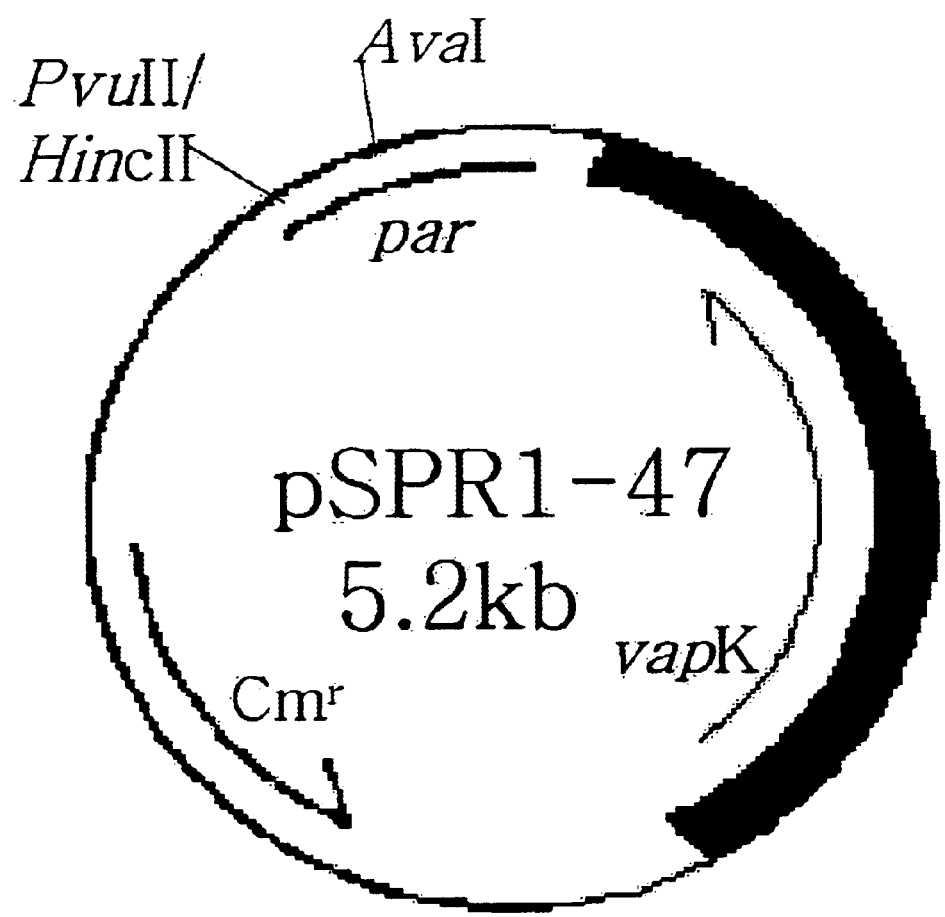
FIG. 7 depicts a restriction enzyme map of the recombinant plasmid vector pSPR1-47 with decreased length comprising the par gene and the reverse-oriented alkaline protease gene vapk.

For the purpose of decreasing the length of the alkaline protease vapk within the recombinant plasmid vector pSPR1, the recombinant plasmid pSPR1 comprising reverse-oriented alkaline protease gene was prepared (FIG. 6). The above recombinant plasmid vector pSPR1 was digested with EcoR I, in which the EcoR I recognition site was positioned at between the alkaline protease gene vapk and the par gene, followed by treating exonuclease Bal31, and annealed with a ligase to prepare the recombinant plasmid vector pSPR1-47 (FIG. 7).

Figure 8:
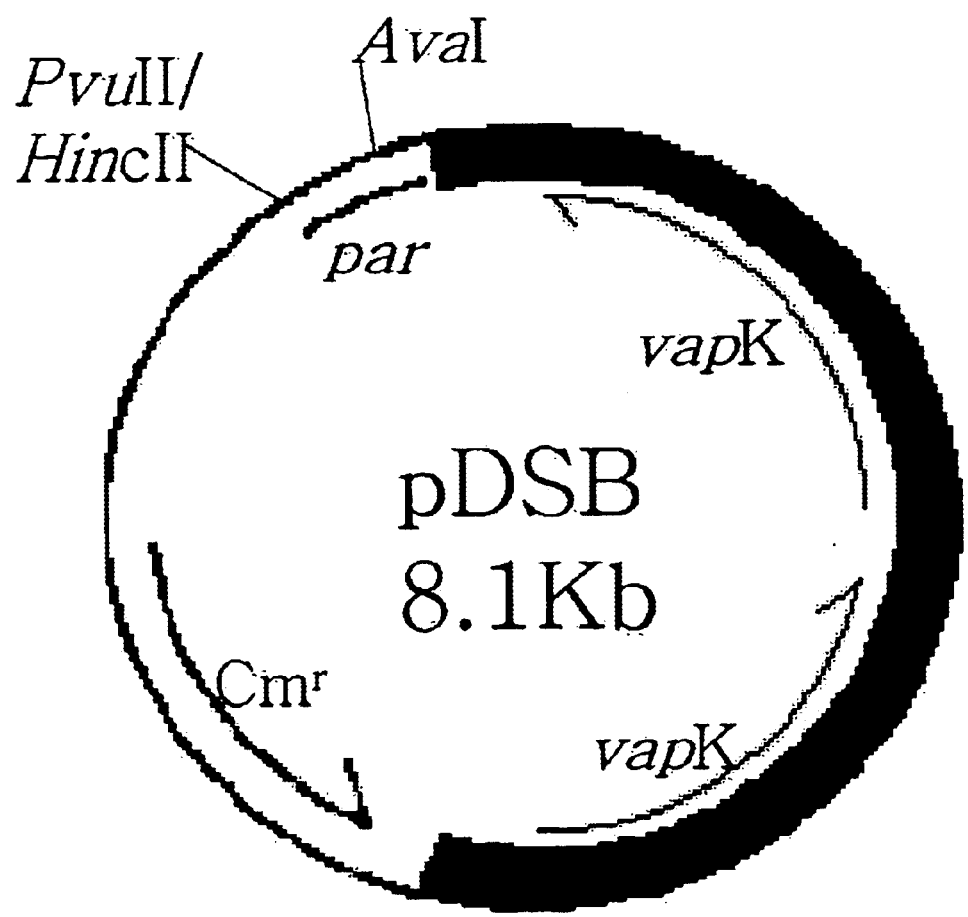
FIG. 8 depicts a restriction enzyme map of the recombinant plasmid vector pDSBCm comprising the vapk gene encoding alkaline protease doubly.
Figure 9:
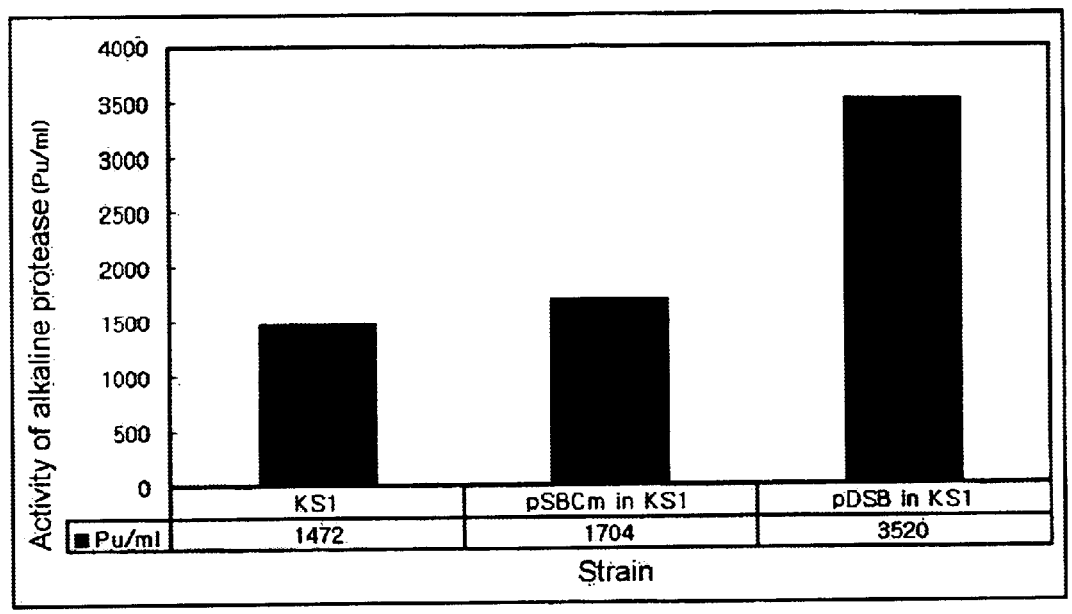
FIG. 9 depicts a result of comparison for alkaline protease activity among *Vibrio metschnikovii* KS1, *Vibrio metschnikovii* pSBCm, and *Vibrio metschnikovii* pDSBCm.

The 2.9 kb alkaline protease gene vapk which was cloned in example 1, was re-inserted into the Hind III recognition site within the recombinant plasmid vector pSPR1-47 to prepare the recombinant plasmid pDSBCm (FIG. 8).

Example 5
Transformation of the Recombinant Plasmid Vector Comprising a Single Alkaline Protease Gene into *E. coli*.

The recombinant plasmid vectors pSBCm, pSP1, pSPR1, pSPR1-47 and pDSBCm comprising the 2.9 kb alkaline protease gene of example 1 or example 2 were introduced into *E. coli* to produce *E. coli* transformants.

After culturing the strain *E. coli* HB101 in a LB medium, 100 mM calcium chloride was added to the fermented culture of *E. coli* HB101. The mixture was stored at 0° C. for 15 minutes and centrifuged to recover *E. coli* HB101. The cell pellet were suspended into a 100 mM calcium chloride solution and stored at 0° C. for 15 minutes. The recombinant plasmid vector pSBCm was added into the suspended solution and stored at 0° C. for 1 hour. The suspended solution was heated at 42° C. for 90 sec and stored at 0° C. for 5 minutes. After insertion of 1 ml LB medium into the suspended solution, the solution was plated on LB agar medium containing 34 μg/ml chloramphenicol and incubated at 30° C. for 24 hours, and the colonies grown were selected.

Example 6
Transformation of *Vibrio metschnikovii* With the Recombinant Plasmid Vector Comprising the Alkaline Protease Gene An electroporation method was used for transformation of *Vibrio metschnikovii* KS1 with the recombinant plasmid vector comprising the alkaline protease gene.

After incubation of *Vibrio metschnikovii* KS1 in a LB medium at 30° C., the grown cells were recovered by centrifugation at 6,000 rpm, 4° C. for 10 minutes and suspended in a H-buffer solution consisting of 200 mM sucrose, 1 mM HEPES and 10% glycerol in the volume ratio of 20:1. After repeating the above process twice, the cells were resuspended into an 80 μl. H-buffer solution. The recombinant plasmid vector was added into the suspended solution and the solution was poured into a 0.2 cm cuvette. The electric power of 1,500V, 10 μF and 200Ω was added to the said cuvette using Gene Pulser II made by Bio-Rad Co. The 600 μl of LB medium was added into the electric power-treated solution and incubated at 30° C. The cultured medium was plated on LB agar medium containing 25 μg/ml of chloramphenicol and the colonies grown were selected.

Example 7
Assay of Expression of the Alkaline Protease from Recombinant *Vibrio metschnikovii* Transformants The activity of alkaline protease was assayed by using a modified Yanagida et al method (1986). Two gram of casein was dissolved in 100 ml of 10 mM sodium carbonate buffer solution, pH 10.5 with heating to produce 2% casein solution. After incubation of *Vibrio metschnikovii* KS1 in a LB medium at 30° C., the supernatant was obtained by centrifugation at 6,000 rpm, 4° C. for 10 minutes and diluted in 10 mM sodium carbonate buffer solution, pH 10.5. Two point five ml of said 2% casein solution was mixed with 0.5 ml of said diluted *Vibrio metschnikovii* solution. The mixture was reacted at 37° C. for 10 minutes, and its reaction was stopped by addition of a solution consisting of 0.22M trichloroacetetic acid, 0.22M acetic acid and 0.22M sodium acetate into the mixture. The mixture was cooling in ice for 15 minutes and the protein precipitate was removed from the mixture by centrifugation at 12,000 rpm, 4° C. for 15 minutes to obtain the supernatant. One milliliter of said supernatant and 9 ml of distilled water were mixed and the optical density of the mixture was determined at 280 mn. The term "1 unit of protease" is defined as the amount that capable to increase the optical density of the reaction solution in the amount of 0.1 after reaction for 10 minutes.

As a consequence, it was verified that the activity of the alkaline protease expressed from a transformed strain *Vibrio metschnikovii* pDSBCm was 2.5 times higher than that of the alkaline protease expressed from the host strain *Vibrio metschnikovii* KS1.

Deposition of the Recombinant Plasmid Vector of the Invention

The strain *Vibrio metschnikovii* pDSBCm comprising the recombinant plasmid vector pDSBCm of the invention was deposited with the Korean Culture Center of Microorganisms, Seoul, Korea, on Jul. 4, 2000, as Accession No. KFCC-11180 and the deposit number was changed into new assigned Accession No. KCCM-10292 at the same center on Jul. 9, 2001 according to the rules of the Budapest treaty.

Industrial Applicability

The production capacity of the alkaline protease for the recombinant plasmid vector transformants comprising the alkaline protease gene dimer prepared by the method according to the present invention is significantly better than that of the prior Vibrio strains. Therefore, the transformed strain *Vibrio metschnikovii* comprising the recombinant plasmid vector pDSBCm of the present invention can be effectively used as an alkaline protease producing strain.

What is claimed is:
1. A recombinant plasmid vector pDSBCm (KCCM-10292) comprising the vapk gene dimmer, which gene encodes an alkaline protease VapK.

2. A method for producing the recombinant plasmid vector pDSBCm of claim 1, comprising inserting the par gene into a recombinant plasmid vector pSBC comprising the vapk gene encoding an alkaline protease to prepare a recombinant plasmid vector pSP1, wherein the par gene has the function of improving the stability of the plasmid vector itself;

orienting the gene vapk of the recombinant plasmid vector pSP1 in reverse direction to prepare a recombinant plasmid vector pSPR1;

digesting the gene between the vapk gene and par gene of pSPR1 with EcoR I, treating with exonuclease Bal31, and ligating them with a ligase to prepare a plasmid vector pSPR1-47 with decreased length; and digesting the plasmid vector pSPR1-47 with Hind III and inserting the gener vapk into the pSPR1-47 excised with Hind III.

3. A transformed host cell comprising the recombinant plasmid vector pDSBCm of claim 1.

4. The transformed host cell according to claim 3, wherein the host cell comprises *Escherchia coli* or *Vibrio metschnikovii*.

5. A method for producing an alkaline protease VapK comprising culturing the host cell of claim 3 and isolating the recombinant protein.

6. A method according to claim 5, wherein the host cell comprises *Escherchia coil* or *Vibrio metschnikovii*.

* * * * *